United States Patent [19]
Chader et al.

[11] Patent Number: 5,617,857
[45] Date of Patent: Apr. 8, 1997

[54] IMAGING SYSTEM HAVING INTERACTIVE MEDICAL INSTRUMENTS AND METHODS

[75] Inventors: Martin D. Chader; Ivan Faul, both of Boulder; Timothy L. Feaver, Louisville; Waldean A. Schulz, Boulder, all of Colo.

[73] Assignee: Image Guided Technologies, Inc., Boulder, Colo.

[21] Appl. No.: 471,279

[22] Filed: Jun. 6, 1995

[51] Int. Cl.$^6$ ................................................. A61B 5/00
[52] U.S. Cl. ...................... 128/653.1; 128/664; 128/899; 128/903
[58] Field of Search ................................. 128/653.1, 664, 128/897, 899, 903; 606/130; 378/37, 205, 207

[56] References Cited

U.S. PATENT DOCUMENTS

| | | |
|---|---|---|
| 4,672,306 | 6/1987 | Thong . |
| 5,005,142 | 4/1991 | Lipchak et al. . |
| 5,332,974 | 7/1994 | Harkins et al. . |
| 5,355,129 | 10/1994 | Baumann . |
| 5,357,953 | 10/1994 | Merrick et al. . |
| 5,383,454 | 1/1995 | Bucholz . |

FOREIGN PATENT DOCUMENTS

2003497  of 0000  Canada .

OTHER PUBLICATIONS

Romilly Bowden, "Smart Instruments to Get Smarter", *Process Engineering*, Nov. 1992, p. 41.
E. Lee Garelick, "Why Calibrate 'Smart' Instruments?", *Intech*, Feb. 1990, pp. 26–27.

*Primary Examiner*—Marvin M. Lateef
*Assistant Examiner*—Shawna J. Shaw
*Attorney, Agent, or Firm*—Townsend and Townsend and Crew LLP

[57] ABSTRACT

The invention provides an improved imaging system and method. The imaging system is of the type having a medical instrument including a source for emitting detectable energy and an instrument body having a work portion. The imaging system further includes detector for detecting the energy and a processor for determining the location of the medical instrument based on the detected energy. Such an imaging system is improved by providing a storage device on or in the medical instrument for storing initialization information, such as the location of the energy-emitting means relative to the instrument body. A transfer device is provided for transferring the initialization information from the storage device to the processor upon connection of the medical instrument to the processor. In this manner, the processor may then configure itself according to the attached instrument so that the system may track the location of the instrument body in three-dimensional space upon detection of the emitted energy.

19 Claims, 5 Drawing Sheets

IMAGING SYSTEM HAVING INTERACTIVE MEDICAL INSTRUMENTS AND METHODS

BACKGROUND OF THE INVENTION

1. Field of the Invention

The invention relates generally to the performance of medical and surgical procedures, particularly with the assistance of an imaging system for correlating the position of medical instruments with scanned images of the body. More particularly, the invention relates to the transfer of stored initialization information from the medical instruments to the imaging system so that the imaging system may be able to configure itself according to the particular type of attached medical instrument.

Determining the precise location of a medical instrument relative to a treatment region is critical in many surgical procedures. Unfortunately, locating the instrument relative to the treatment region can often be difficult, particularly when the treatment region is within the patient and out of the surgeon's view. To assist in locating both the treatment region and the medical instrument, a variety of imaging systems have been proposed including computerized tomographic (CT) scans, magnetic resonance imaging (MRI) scanning, positron emission tomographic (PET) scanning, and the like. Although generally successful in producing detailed images of the body, one difficulty experienced with such systems is the need to correlate the position of a therapeutic or a surgical instrument during treatment with the produced diagnostic image of the treatment region so that the surgeon can correctly position the instrument at the treatment region.

One promising imaging system for detecting the position of the medical instrument relative to a diagnostic image of the treatment region is described in U.S. Pat. No. 5,383,454, the disclosure of which is herein incorporated by reference. Briefly, such a system provides a plurality of discrete energy-emitting elements on the medical instrument which are detected by a receiver near the operative site. With the use of a computer, the detected signals are used to determine the location of the medical instrument relative to the receiver. The patient's position is initialized and/or the patient is provided with a series of energy-emitting devices so that the location of the patient relative to the receiver is known. The computer is then able to track the location of the medical instrument relative to the patient in real-time. Such information can then be correlated with previously produced images of the patient's body which are produced on a screen. In this way, as the surgeon moves the instrument to the treatment region, an image can be produced on the screen showing a marker indicative of the instrument position relative to the previously produced image of the body (which corresponds to the actual position of the treatment region relative to the medical instrument).

One particular advantage of such a system is that it may be configured to track a wide variety of medical instruments simply by reinitializing the imaging system each time a new instrument is attached so that the system will be properly configured according to the attached instrument. Such initialization information can include, for example, the number of energy-emitting elements on the instrument, the location of the energy-emitting elements relative to a work portion of the medical instrument, and the like. Usually, such information is manually entered into the computer, such as by use of a keyboard or the like. However, manually initializing the imaging system in such a manner suffers from a number of serious drawbacks. For example, the initialization information may be improperly input into the system which may result in the improper tracking of the medical instrument. Another drawback is that the medical instrument may be removed from the system following initialization and replaced with another instrument. If the system is not reinitialized, improper tracking of the new instrument may result. In a further drawback, the manual entry of such initialization information is time-consuming and nay increase the length of the medical procedure.

Hence, for these and other reasons it would be desirable to provide an improved imaging system that would overcome or greatly reduce all or at least some of these drawbacks. In particular, it would be desirable to provide improvements in the initialization of the imaging system so that initialization information can correctly and efficiently be input into the system. Such improvements should also provide improved safety by ensuring that the imaging system is properly initialized upon connection of each type of medical instrument.

2. Brief Description of the Background Art

As previously described, U.S. Pat. No. 5,383,454 discloses a system for indicating the position of a surgical probe on a previously produced image of the patient's body.

Canadian Patent Application Serial No. 2003497 describes a system for visualizing an image of a hand held probe relative to previously produced images of the patient's body. The complete disclosure of this application is incorporated herein by reference.

U.S. Pat. No. 4,672,306 describes an electronic probe assembly that provides previously recorded data as to probe identification and optimum compensation tuning of the probe to a connected "intelligent" test and measurement device.

Romilly Bowden, *Smart instruments to get smarter, Process Engineering*, November 1992, p. 41, describes a hand held communicator for ensuring compatibility between different manufacturer's instruments.

E. Lee Garelick, *Why calibrate "smart" instruments?, Intech*, February 1990, pp. 26–27, describes the calibration of "smart" instruments.

SUMMARY OF THE INVENTION

The invention provides an improved imaging system of the type having a medical instrument that includes means for emitting detectable energy and an instrument body having a work portion. The imaging system further includes a means for detecting the energy and a processor for determining the location of the medical instrument based on the detected energy. Such an imaging system is improved by providing a means on or in the medical instrument for storing initialization information, such as the location of the energy-emitting means relative to the instrument body. Further provided is a means for transferring the initialization information from the storing means to the processor upon connection of the medical instrument to the processor. In this way, the processor may be initialized upon connection of the medical instrument to the processor without requiring the manual entry of initialization information into the processor. With such information, the processor may then determine the location of the instrument body in three-dimensional space upon detection of the energy emitted from the medical instrument during a medical procedure. Preferably, the storing means will comprise an electronic memory chip, such as an EPROM, PROM, or PAL chip. The energy-emitting means will usually comprise a plurality of energy-emitting elements.

In one particular embodiment, the storing means is integrally formed with the instrument body and includes information relating to the location of the work portion relative to the energy-emitting means. In this way, the medical instrument may be formed as a single integrated device having the chip embedded therein.

In an alternative embodiment, the medical instrument includes a removable attachment having the energy-emitting means and the storing means. In one aspect of this embodiment, the attachment may be connected to a wide variety of instrument bodies having different geometric configurations. In such a case, the storing means will preferably include information indicating that the storing means is included in the attachment (as opposed to a fully integrated instrument) so that the processor may be able to determine that the instrument body is being used with the attachment. The processor will then preferably prompt the user to enter appropriate initialization information relating to the particular type of instrument body. Optionally, the storing means may include information relating to the particular configuration of the attachment so that different types of attachments may be employed without having to manually enter initialization information regarding the configuration of the attachment.

In another aspect, a means is provided for allowing the attachment to be connected to only selected types of instrument bodies, such as with instruments having a work portion that is at the same location relative to where the instrument body attaches to the attachment. With such a configuration, the storing means will include information relating to the location of the energy-emitting elements relative to the selected type of instrument body so that the processor may be initialized for the selected type of instrument body.

In still a further aspect, a means is provided for indicating the particular type of instrument that is connected to the attachment so that upon connection of the attachment to the instrument body, the processor will know which type of instrument body is connected. Preferably, the indicating means will comprise an electrical circuit that is formed upon connection of the medical instrument to the attachment. A characteristic of the circuit is then detected to determine the particular type of attached instrument. The processor will preferably further include a means for correlating the location of the work portion on the instrument body relative to the energy-emitting elements on the attachment. In this manner, the processor may be able to correlate information regarding the particular type of instrument body with the configuration of the attachment so that the processor will be properly initialized.

In yet another aspect, the medical instrument will preferably include means for detecting when the attachment has been connected to the instrument body and then subsequently removed. In such an event, the system will not operate unless new initialization information is input, thereby preventing reconnection of the attachment to another type of instrument body without reinitializing the system.

In another aspect of the system, a reference frame is provided and is in communication with the processor. The reference frame includes at least three energy-emitting units for defining a coordinate system. A means is provided for storing the information identifying the reference frame upon connection of the reference frame to the processor so that the processor will know that it has been connected to the reference frame.

The invention provides an improved method of the type wherein the location of an instrument body of a medical instrument is determined by detecting energy emitted from an energy-emitting source associated with the medical instrument and processing in a processor the detected information. The improvement comprises connecting the medical instrument to the processor and transferring stored electronic initialization information from the medical instrument to the processor, particularly regarding the location of the energy-emitting source relative to the medical instrument. With the processor, the location of the instrument body in three-dimensional space may then be determined based at least in part on the detected information and the stored information.

In one alternative aspect, the energy-emitting source is integrally formed with the instrument body. With such a configuration, electronic information is transferred from the medical instrument to the processor regarding the location of the energy-emitting source relative to a work portion of the instrument body. In an alternative aspect, the medical instrument includes an attachment having the energy-emitting source and the stored electronic information. The attachment is then removably attached to the instrument body.

In one particular aspect, electronic information is transferred from the attachment to the processor indicating that the attachment has been connected to the instrument body. The user may then optionally manually enter into the processor information identifying the type of instrument body that is connected to the attachment.

In an alternative aspect, the method provides for selectively preventing connection of the attachment to the instrument body based on the stored information in the attachment and the type of instrument body. In this way, the attachment may only be connected to certain types of instrument bodies (such as those having a common geometric configuration) so that the stored information will correspond to the connectable types of instrument bodies. Electronic information regarding the location of the energy-emitting source relative to a work portion on the instrument body may then be transferred from the attachment to the processor.

In still a further alternative aspect, the particular type of instrument body is detected upon connection of the attachment to the instrument body. With the processor, the location of a work portion of the instrument body relative to the energy-emitting source is determined based on the type of instrument body that is connected to the attachment. Preferably, the detecting step will comprise forming an electrical circuit upon connection of the attachment to the instrument body and measuring a characteristic of the circuit when current is passed therethrough.

In one particular aspect of the method, a reference frame is placed in communication with the processor, with the reference frame having at least three energy-emitting units. Electronic information identifying the reference frame is then transferred to the processor upon connection of the reference frame to the processor.

The invention provides an exemplary method for introducing a medical instrument to a treatment site. The method comprises providing the instrument with an instrument body, an energy-emitting source, and stored information regarding the location of the energy-emitting source relative to the instrument body. An identifiable portion of the instrument body is then positioned at a known location and energy is emitted from the energy-emitting source. The emitted energy is then detected while the portion is at the known location. Based on the detected energy, the location of the energy-emitting source relative to the identifiable portion of the instrument body is determined. The determined location of the energy-emitting source relative to the identifiable portion of the instrument body is then compared with the stored information regarding the location of the energy source relative to the identifiable portion. In this way, a verification procedure is provided to assist in assuring that the determined location of the energy source relative to the instrument body is the same as the stored information regarding the location of the energy source. Otherwise, an error signal or an alarm will be produced to alert the user of a potential miscalibration or other problem existing in the imaging system.

DESCRIPTION OF THE SPECIFIC EMBODIMENTS

Figure 1:
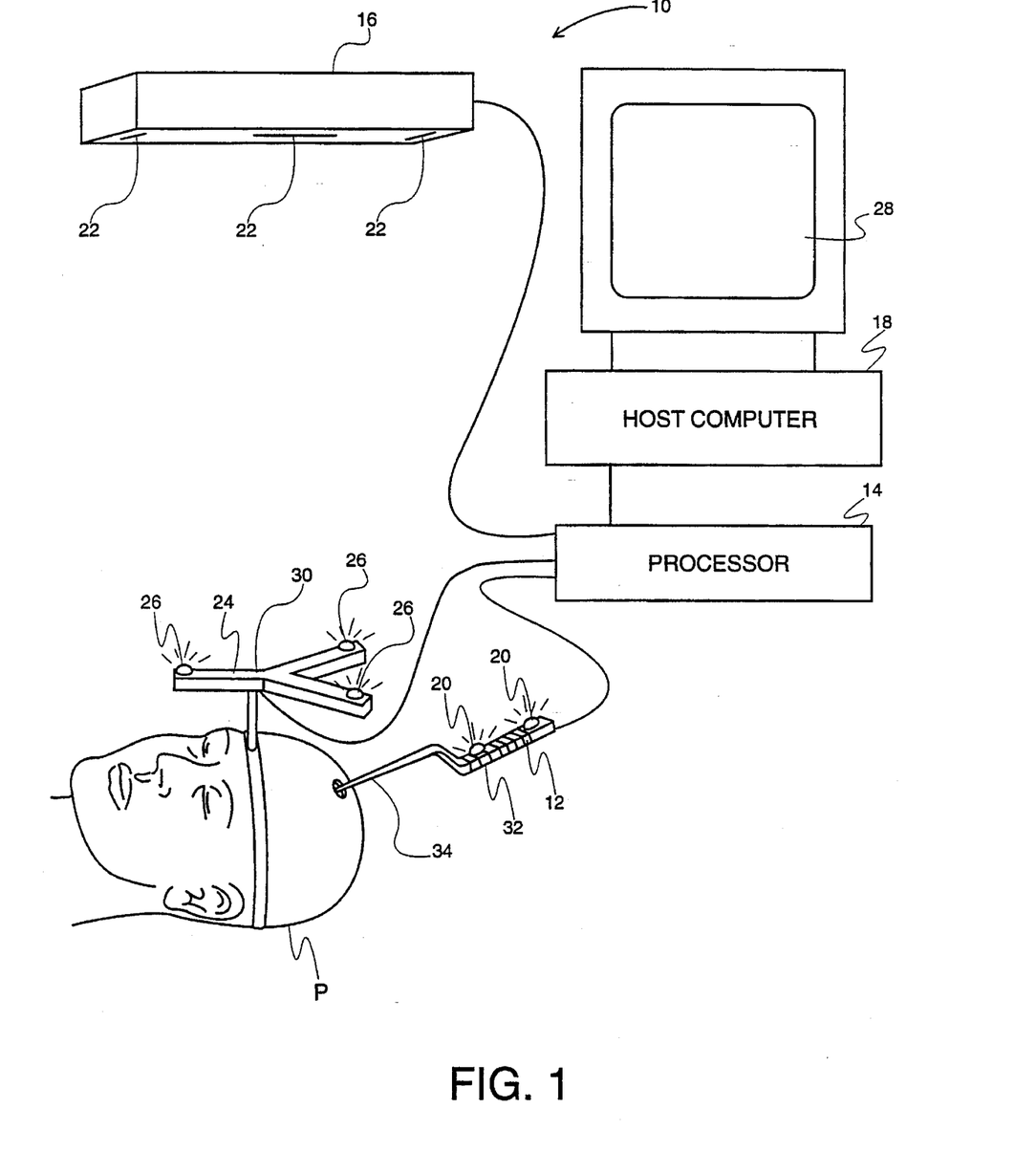
FIG. 1 illustrates an exemplary embodiment of an imaging system constructed in accordance with the principles of the present invention.

Referring now to FIG. 1, an exemplary embodiment of an imaging system 10 will be described. The imaging system 10 includes a medical instrument 12 that is connected to a processor 14. Also connected to the processor 14 is a sensor assembly 16, a host computer 18, and a reference frame 24. The medical instrument 12 includes a plurality of energy-emitting elements 20 for emitting energy that may be detected by sensors 22 on the sensor assembly 16 to determine the location of the energy-emitting elements 20 in three-dimensional space. The reference frame 24 is provided with a plurality of energy-emitting elements 26 and is securely attached to a patient P. An exemplary reference frame is a Dynamic Reference Frame™ (DRF), commercially available from Image Guided Technologies, Boulder, Colorado.

Stored in the host computer 18 are previously obtained images of the patient P, such as those obtained from an MRI scan. As described in U.S. patent application Ser. No. 5,383,454, previously incorporated by reference, the location of the medical instrument 12 may be tracked relative to the patient P in real-time and correlated with the previously produced images of the patient's body which are displayed on a screen 28 of the host computer 18. To track the medical instrument 12 in this manner, the medical instrument 12 is advanced into the patient P while the energy-emitting elements 20 are energized and detected by the sensor assembly 16. The elements 26 on the reference frame 24 are also energized and detected so that the location of the medical instrument 12 relative to the patient P may be tracked by the processor 14, even when the patient P is moved. The location information in the processor 14 is then correlated with the previously produced images of the patient's body in the host computer 18 so that as the surgeon moves the medical instrument 12 to a treatment region, an image can be produced on the screen 28 showing a position marker of the instrument 12 relative to the previously produced images of the body.

One exemplary feature of the imaging system 10 is that a wide variety of medical instruments may be used with the system 10, such as those described in copending U.S. patent application Ser. No. 08/431,085, filed Apr. 28, 1995, the complete disclosure of which is herein incorporated by reference. When using such medical instruments, the processor 14 is first initialized so that the processor 14 is provided with information regarding the configuration of the attached medical instrument. For example, the medical instrument 12 will usually comprise an instrument body 32 having a work portion 34 for performing the medical procedure. In order to display the position of the work portion 34 on the screen 28, the processor 14 must know the location of the work portion 34 relative to the energy-emitting elements 20.

To provide such initialization information, the invention in one particularly preferable embodiment provides a memory module 36 (see FIG. 2) associated with the medical instrument 12 so that upon attachment of the medical instrument 12 to the processor 14, initialization information in the memory module 36 may be transferred to the processor 14 to initialize the processor 14.

Figure 2:
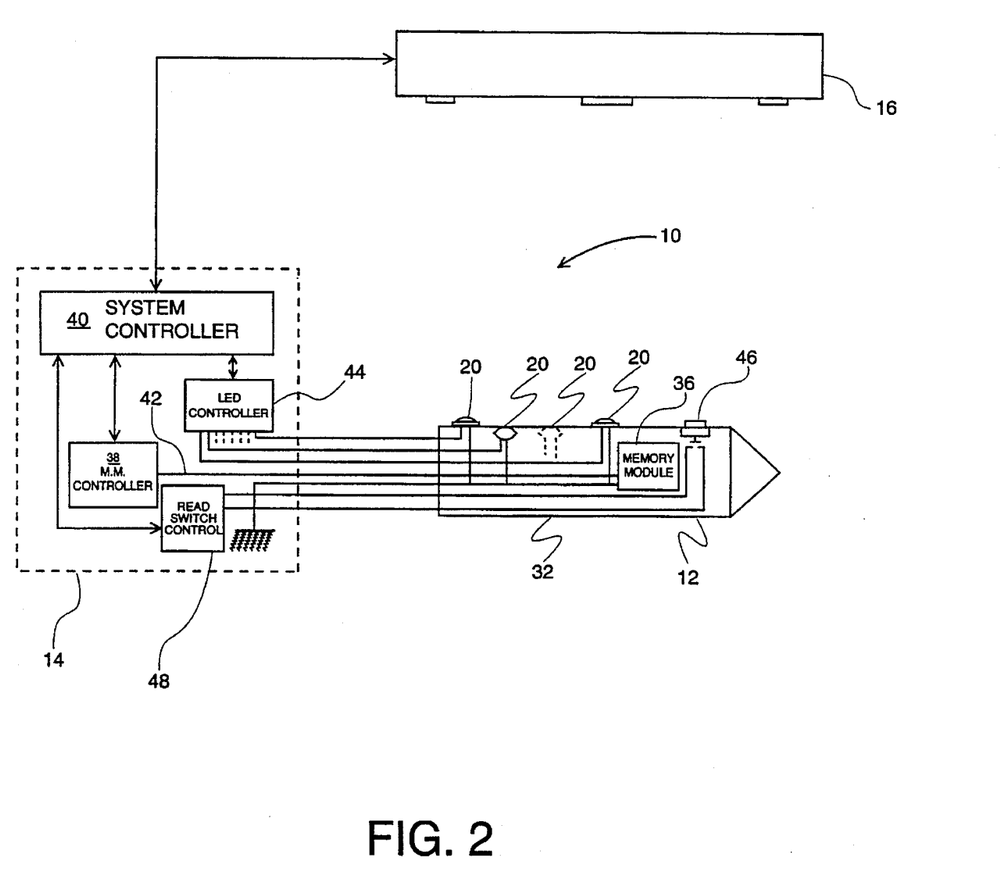
FIG. 2 is a schematic of the electronics employed in the imaging system of FIG. 1.

Referring to FIG. 2, the imaging system 10 is illustrated schematically and will be described in greater detail. As previously described, the medical instrument 12 includes the memory module 36. The memory module 36 may be integrally formed with the instrument body 32 or may be included in a separate attachment as will be described in greater detail hereinafter. The memory module 36 will preferably be constructed of a "one-wire" EPROM computer chip, commercially available from Dallas Semiconductor. The EPROM chip may be preprogrammed with a variety of initialization information including the serial number of the instrument, the instrument type or part number, the number of buttons on the instrument, the number of energy-emitting elements on the instrument, the local XYZ coordinates of the work portion or other reference location on the instrument, the unit direction vectors of the "longitudinal direction" of the instrument, the unit direction vectors of the "transverse direction" of the instrument, the local XYZ coordinates for each of the energy-emitting elements, and the like.

When the instrument 12 is connected to the processor 14, the memory module 36 is placed in communication with a memory module controller 38 in the processor 14. In turn, the memory module controller 38 is in communication with a system controller 40 in the processor 14. To retract the initialization information from the memory module 36, the system controller 40 sends a signal to the memory module controller 38 which sends an appropriate command sequence along a control line 42 which will prompt the memory module 36 to send some or all of its programmed information back to the controller 38 over the control line 42. Hence, the processor 14 will be able to recognize the characteristics of the medical instrument 12 upon connection of the instrument to the processor 14 without requiring the manual entry of the instrument's type or other configuration information into the processor 14.

The energy-emitting elements 20 will preferably comprise light-emitting diodes (LEDs) that are appropriately positioned on the instrument body 32 so that they may be detected by the sensor assembly 16. Other suitable energy-emitting elements are described in copending U.S. application Ser. No. 08/431,085. The instrument 12 will usually be provided with two or more energy-emitting elements 20, and the number of elements 20 along with their location on the instrument body 32 will be stored in the memory module 36. Each of the energy-emitting elements 20 is placed in communication with an LED controller 44 in the processor unit 14. In turn, the LED controller 44 is in communication with the system controller 40 so that emission of energy from the elements 20 may be precisely controlled.

The medical instrument 12 may optionally be provided with one or more buttons 46 that is placed in communication with a read switch controller 48 when the instrument 12 is connected to the processor 14. When the button 46 is depressed, the read switch controller 48 signals the system controller 40 to perform a specific function. In this way, the button 46 and the controller 48 may be employed to perform a variety of functions, such as controlling the acquisition of data by the imaging system or driving applications software in the host computer 18. For example, the button 48 may be depressed to obtain a specific coordinate at the point where the button 48 is depressed. Alternatively, the medical instrument 12 may be placed over a particular portion of the patient P and the button 48 depressed to produce an image of the selected portion on the screen 28.

As previously described, the memory module 36 may be integrally formed with the instrument body 32 or may be included in a separate attachment that may be removably connected to the instrument body 32. When integrally formed with the instrument body 32, the memory module 36 will preferably be programmed to include all of the previously described initialization information, including both the position and orientation of the instrument's distal tip or work portion. In this way, each time the instrument 12 is attached to the processor 14, information may be transferred to the processor 14 so that the system 10 will be properly configured for the attached instrument 12.

Figure 3:
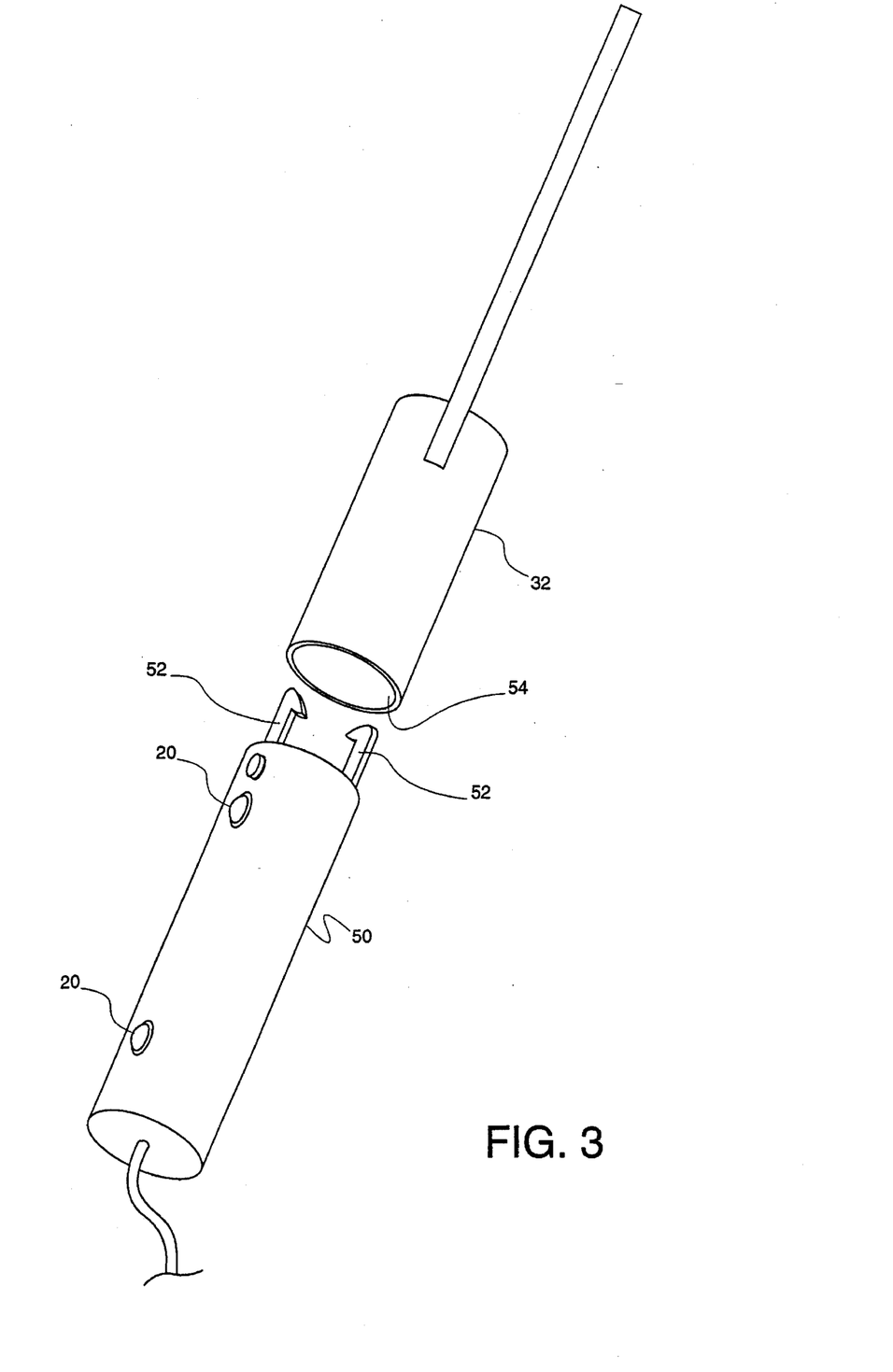
FIG. 3 illustrates an alternative embodiment of a medical instrument having an attachment for housing a memory module according to the present invention.

Removable attachment of the memory module 36 to the instrument body 32 will be described with reference to FIG. 3. In FIG. 3, the memory module 36 is included in an attachment 50 that may be removably attached to the instrument body 32. The attachment 50 further includes the energy-emitting elements 20 and may optionally include one or more buttons 46. The attachment 50 includes a pair of tabs 52 that are received within an aperture 54 of the instrument body 32. Included in the aperture are a pairs of knobs (not shown) for engaging the tabs 52 when the tabs are inserted into the aperture 54 and rotated. Although shown with tabs 52, the attachment 50 may alternatively be removably attached to the instrument body 32 by a variety of other fasteners such as those described in copending U.S. patent application Ser. Nos. 08/431,085 and 08/436,711, the disclosures of which are herein incorporated by reference. The attachment 50 may be used in connection with any type of instrument body 32 or with selected types of instrument bodies as described hereinafter.

In one aspect, the attachment 50 may be configured so that it may be attached to any type of rigid instrument body. In such a case, the memory module 36 will include information that may be transferred to the processor 14 indicating that the medical instrument 12 includes an attachment (rather than being a fully integrated instrument). In such a case, the memory module 36 will preferably transfer such information as the number and specific configuration of the energy-emitting elements 20 on the attachment 50. When receiving such information, the software in the processor 14 will preferably prompt the user to enter initialization information into the processor 14 relating to the type of the attached instrument body 32.

Alternatively, the attachment 50 may be configured so that it will be connectable only with instrument bodies having a common geometry, e.g. such as with instruments having work portions in the same location relative to a point at which the instrument body 32 connects to the attachment 50. The attachment 50 may be keyed so that it may be used only with certain classes of instruments that are suitable for use with the information programmed in the memory module 36 of the mating attachment 50. When the attachment 50 is configured to be connected to only selective instrument bodies, the memory module 36 will preferably include initialization information common to each type of instrument body in the defined class as well as information relating to the particular configuration of the attachment 50. In this way, initialization of the processor 14 will proceed in essentially the same manner as the fully integrated instrument as previously described.

In a further exemplary alternative, the imaging system 10 will be constructed to detect the particular type of instrument body 32 that is connected to the attachment 50. Preferably, such detection will be accomplished by an electrical circuit that is formed upon connection of the attachment 50 to the instrument body 32. A characteristic of the circuit (such as inductance, resistance, current, voltage, or the like) may be detected to determine the particular type of attached instrument body 32. With such a configuration, the memory module 36 may optionally be removed since the processor 14 will know the particular type of instrument that is connected to the attachment 50 (assuming each attachment used with the system has the same configuration). If different attachment configurations are employed, the memory module 36 may be included and will be configured to include information relating to the attachment configuration, e.g. such as the number and location of the energy-emitting elements 12 relative to the attachment 50.

Figure 4:
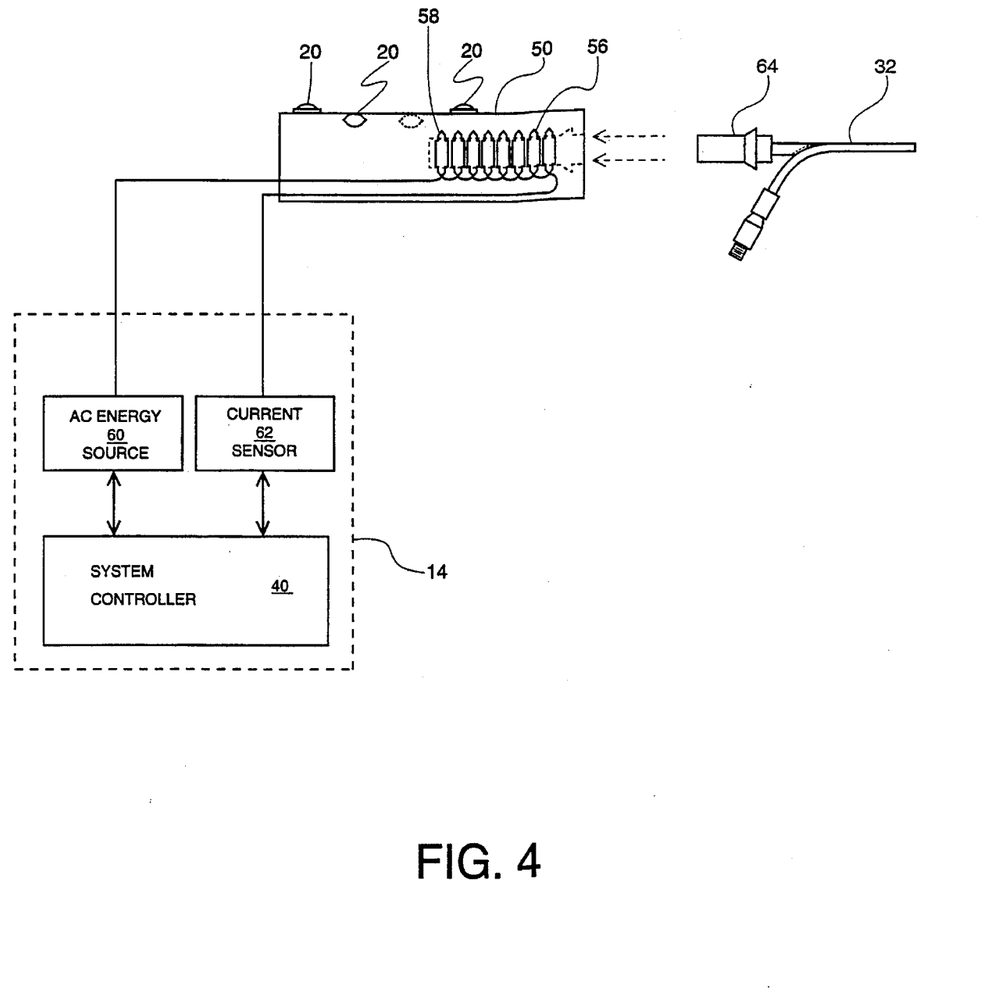
FIG. 4 is a schematic of an exemplary sensing circuit for sensing the type of instrument body that is connected to an attachment according to the present invention.

One exemplary embodiment of such a sensing circuit 56 is shown in FIG. 4. The circuit 56 includes a precisely wound coil 58 that is preferably enclosed in plastic that forms the attachment 50. The coil 58 is connected to an AC energy source 60 which in turn is in communication with the system controller 40. The instrument body 32 is provided with a mounting adapter 64 that may be slid into the coil 58 as shown in phantom line. The adapter 64 is constructed at least partially of a ferrous material. When the adapter 64 is placed within the coil 58 and current is passed through the coil 58, the inductance of coil 58 is changed and may be detected by a current sensor 62. The ferrous content and/or the length or cross-section of the adapter 64 may be varied to cause coil 58 to assume a different inductance. In this way, the adapter 64 may be tailored to produce a different inductance for each type of instrument body 32.

Based on the amount of current sensed by the current sensor 62, the system controller 40 is able to determine the particular type of attached instrument body 32. The processor 14 may then be configured according to the attached medical instrument.

Other circuit designs for detecting the type of attached instrument body 32 are possible, such as by placing a resistor in the instrument body 32 (or an attached adapter), with the resistor closing a circuit when the attachment 50 is connected to the instrument body 32. Each type of instrument body 32 will include a different sized resistor so that by sensing the amount of current passing through the circuit, the type of instrument body 32 may be detected.

When employing the attachment 50, the imaging system 10 will preferably be constructed to detect when the attachment 50 has been fully connected to the instrument body 32 and has then been subsequently removed. If such a removal has been detected, the system 10 will preferably be configured so that it will not be operable unless reinitialized. In this way, improper initialization of the system 10 will be prevented in the event that the attachment 50 is subsequently connected to a different instrument body 32 without reinitializing the system according to the newly attached instrument body. Such a feature may be accomplished in a variety of ways, such as by providing a Hall sensor, a mechanical switch, or the like to detect detachment of the instrument body 32 from the attachment 50. Alternatively, detachment may be detected by the breaking of an electrical circuit formed between the attachment and the instrument body. In a further alternative, the attachment 50 may be provided with a break-away connector that disenables the attachment 50 after removal from the instrument body 32. In this way, the attachment 50 is prevented from being reconnected to another instrument.

In a further aspect of the imaging system 10, the processor 14 may be configured so that it will not operate with medical instruments not having a memory module 36, or the processor 14 may alternatively be configured as part of an encryption scheme so that the processor 14 will not recognize data returned from the memory module 36 (or from associated electronics in the instrument) unless the memory module 36 has been processed according to the preprogrammed encryption scheme. In this manner, the manufacturer may ensure that an inferior or incorrectly programmed attachment will not be used with its processor or instrument bodies.

Referring back to FIG. 1, the reference frame 24 may optionally be provided with a memory module similar to the memory module 36 of the medical instrument 12. When the reference frame 24 is connected to the processor 14, information from the memory module will be transferred to the processor so that the processor 14 may treat the reference frame 24 as a coordinate system rather than an instrument to be tracked.

Figure 5:
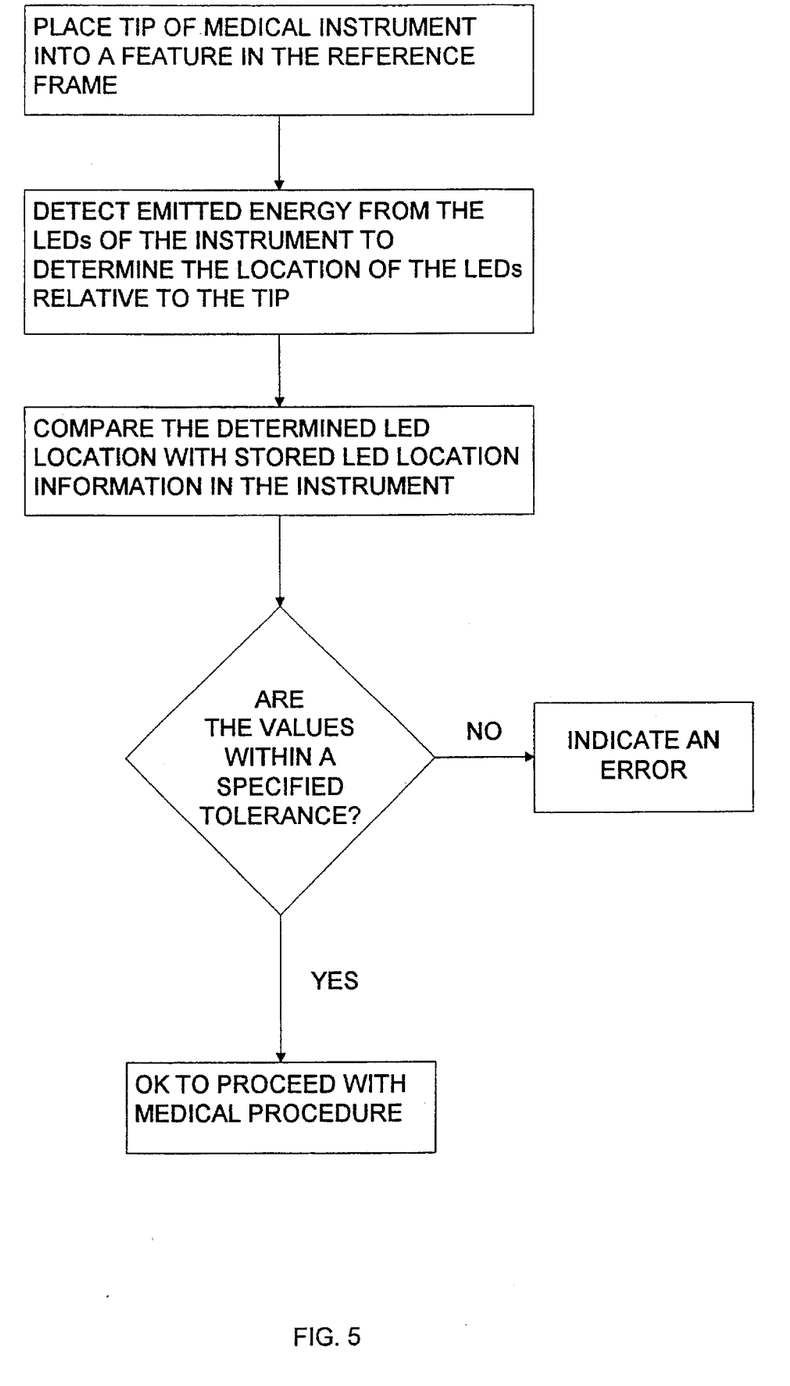
FIG. 5 is a flow chart illustrating an exemplary method for verifying the accuracy of the imaging system of FIG. 1.

The memory module 36 of the medical instrument 12 can alternatively be employed to verify the accuracy of the imaging system 10 as illustrated in FIG. 5. As previously described, the memory module 36 contains data on the dimensions and features of the medical instrument 12. Such data is preprogrammed into the memory module 36 during initial calibration of the medical instrument at the time of manufacture. Such information is transferred to the processor 14 and is used to initialize the system 10. In some cases (such as when the attachment 50 is employed with instrument bodies having different geometric configurations), some initialization information may be manually entered into the processor 14 as previously described. In the event that the instrument is becomes damaged or something in the imaging system varies, the data measured by the system 10 can be compared with the embedded calibration data in the memory module 36 (or the manually input initialization information) to determine any discrepancies. To perform such a comparison, the tip of the medical instrument 12 is initially placed into a feature 30 in the reference marker 24. The medical instrument 12 is then pivoted about the feature 30 while a series of measurements are taken by the sensor assembly 16 and transferred to the processor 14. Since the tip of the medical instrument 12 is at a known location when within the feature 30 (as defined by the reference frame 24), the measured signals can be processed in the processor 14 to determine the location of the LEDs 20 relative to the tip. These values can then be compared with the stored LED location information from the memory module 36 (or the manually input initialization information). If the measured values fall beyond certain tolerances when compared to the stored or manually entered data, an error signal can be produced indicating the discrepancy. The imaging system 10 and/or the medical instrument 12 can then be further evaluated to determine the discrepancy.

Although the foregoing invention has been described in some detail by way of illustration and example, for purposes of clarity of understanding, it will be obvious that certain changes and modifications may be practiced within the scope of the appended claims.

What is claimed is:

1. An improved imaging system of the type having a medical instrument including means for emitting detectable energy and an instrument body having a work portion, the imaging system further including means for detecting the energy and a processor for determining the location of the medical instrument based on the detected energy, wherein the improvement comprises:

means on or in the medical instrument for storing information relating to the location of the energy-emitting means relative to the instrument body;

means for transferring the location information from the storing means to the processor upon connection of the medical instrument to the processor, wherein the processor may determine the location of the instrument body in three-dimensional space upon receipt of the location information and upon detection of the emitted energy, wherein the medical instrument further includes an attachment having the storing means and means for emitting detectable energy; and means for indicating the type of instrument body that is connected to the attachment, the indicating means being formed upon connection of the attachment to the instrument body, and wherein the processor includes means for correlating the location of the work portion relative to the energy-emitting elements based on the type of instrument body that is connected to the attachment.

2. The system of claim 1, wherein the storing means comprises an electronic memory chip.

3. The system of claim 1, wherein the energy-emitting means comprises a plurality of energy-emitting elements.

4. The system of claim 3, wherein the storing means is included within the instrument body and includes information relating to the location of the work portion relative to the energy-emitting means.

5. The system of claim 3, wherein the medical instrument includes a removable attachment having the energy-emitting means and the storing means.

6. The system of claim 5, wherein the storing means includes information indicating that the storing means is included in the attachment, wherein the processor may determine that the instrument body is being used with the attachment.

7. The system of claim 1, wherein the means for determining the type of instrument body comprises an electrical circuit that is formed upon connection of the attachment to the instrument body, whereby a characteristic of the circuit may be detected to indicate the type of instrument body.

8. The system of claim 5, further comprising means for attaching the attachment to only selected types of instrument bodies, and wherein the storing means includes information relating to the location of the energy-emitting elements relative to the selected type of instrument body.

9. The system of claim 1, wherein the system further includes a reference frame in communication with the processor, the reference frame having at least three energy-emitting units and having means for storing information identifying the reference frame upon connection of the reference frame to the processor.

10. An improved method of the type wherein the location of an instrument body of a medical instrument is determined by detecting energy emitted from an energy-emitting source associated with the medical instrument and processing in a processor the detected information, wherein the improvement comprises:

connecting the medical instrument to the processor;

transferring stored electronic information from the medical instrument to the processor regarding the location of the energy-emitting source relative to the medical instrument;

determining with the processor the location of the instrument body in three-dimensional space based at least in part on the detected information and the stored information;

wherein the medical instrument further includes an attachment having the energy-emitting source and the stored electronic information, and further comprising removably attaching the attachment to the instrument body; and further comprising detecting the type of instrument body upon connection of the attachment to the instrument body and determining the location of a work portion of the instrument body relative to the energy-emitting source based on the type of instrument body that is connected to the attachment.

11. The method of claim 10, wherein the energy-emitting source is included within the instrument body, and wherein the transferring step further includes transferring electronic information from the medical instrument to the processor regarding the location of the energy-emitting source relative to a work portion of the instrument body.

12. The method of claim 10, wherein the transferring step further comprises transferring from the attachment to the processor electronic information indicating that the attachment is connected to the instrument body, and further comprising manually entering into the processor information identifying the type of instrument body that is connected to the attachment.

13. The method of claim 10, further comprising selectively preventing connection of the attachment to the instrument body based on the stored information in the attachment and the type of instrument body.

14. The method of claim 13, wherein the transferring step further comprises transferring to the processor electronic information regarding the location of the energy-emitting source relative to a work portion on the instrument body.

15. The method of claim 10, wherein the detecting step comprises forming an electrical circuit upon connection of the attachment to the instrument body and measuring a characteristic of the circuit when current is passed therethrough.

16. The method of claim 10, further comprising placing a reference frame in communication with the processor, the reference frame having at least three energy-emitting units, and further comprising transferring to the processor electronic information identifying the reference frame upon connection of the reference frame to the processor.

17. An improved imaging system of the type having a medical instrument including means for emitting detectable energy and an instrument body having a work portion, the imaging system further including means for detecting the energy and a processor for determining the location of the medical instrument based on the detected energy, wherein the improvement comprises:

means on or in the medical instrument for storing information relating to the location of the energy-emitting means relative to the instrument body; and means for transferring the location information from the storing means to the processor upon connection of the medical instrument to the processor, wherein the processor may determine the location of the instrument body in three-dimensional space upon receipt of the location information and upon detection of the emitted energy;

wherein the medical instrument includes a removable attachment having the energy-emitting means and the storing means, wherein the storing means includes information indicating that the storing means is included in the attachment, and wherein the processor may determine that the instrument body is being used with the attachment.

18. An improved method of the type wherein the location of an instrument body of a medical instrument is determined by detecting energy emitted from an energy-emitting source associated with the medical instrument and processing in a processor the detected information, wherein the improvement comprises:

connecting the medical instrument to the processor;

transferring stored electronic information from the medical instrument to the processor regarding the location of the energy-emitting source relative to the medical instrument; and determining with the processor the location of the instrument body in three-dimensional space based at least in part on the detected information and the stored information;

wherein the medical instrument further includes an attachment having the energy-emitting source and the stored electronic information, and further comprising removably attaching the attachment to the instrument body; and wherein the transferring step further comprises transferring from the attachment to the processor electronic information indicating that the attachment is connected to the instrument body, and further comprising manually entering into the processor information identifying the type of instrument body that is connected to the attachment.

19. An improved method of the type wherein the location of an instrument body of a medical instrument is determined by detecting energy emitted from an energy-emitting source associated with the medical instrument and processing in a processor the detected information, wherein the improvement comprises:

connecting the medical instrument to the processor;

transferring stored electronic information from the medical instrument to the processor regarding the location of the energy-emitting source relative to the medical instrument; and determining with the processor the location of the instrument body in three-dimensional space based at least in part on the detected information and the stored information;

wherein the medical instrument further includes an attachment having the energy-emitting source and the stored electronic information, and further comprising removably attaching the attachment to the instrument body; and further comprising selectively preventing connection of the attachment to the instrument body based on the stored information in the attachment and the type of instrument body.

* * * * *